(12) United States Patent
Shi

(10) Patent No.: US 6,369,245 B1
(45) Date of Patent: Apr. 9, 2002

(54) EPOXIDATION OF OLEFINS

(75) Inventor: Yian Shi, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/663,390

(22) Filed: Aug. 10, 2000

Related U.S. Application Data
(60) Provisional application No. 60/148,904, filed on Aug. 13, 1999.

(51) Int. Cl.[7] .............................................. C07D 301/12
(52) U.S. Cl. ...................................................... 549/531
(58) Field of Search ......................................... 549/531

(56) References Cited

U.S. PATENT DOCUMENTS

| | | | |
|---|---|---|---|
| 4,902,820 A | | 2/1990 | Zoeller |
| 5,403,549 A | | 4/1995 | McNeil et al. |
| 5,414,078 A | | 5/1995 | Liotta et al. |
| 5,859,265 A | * | 1/1999 | Muller et al. ................ 549/531 |
| 6,060,610 A | * | 5/2000 | Arca et al. ................... 549/531 |
| 6,160,137 A | * | 12/2000 | Tsuji et al. .................. 549/523 |
| 6,160,138 A | * | 12/2000 | Escrig et al. ................ 549/531 |
| 6,194,591 B1 | * | 2/2001 | Grey et al. .................. 549/533 |
| 6,225,482 B1 | * | 5/2001 | Drauz et al. ................. 549/525 |

OTHER PUBLICATIONS

Tu et al., *J. Am. Chem. Soc.*, 1996, 118, 9806–9807.
Wang et al., *J. Am. Chem. Soc.*, 1997, 119, 11224–11235.
Wang et al., *J. Org. Chem.*, 1997, 62, 2328–2329.
Wang et al., *J. Org. Chem.*, 1997, 62, 8622–8623.
Kurihara et al., *Tet. Lett.*, 1994, 35, 1577–1580.
Denmark et al., *J. Org. Chem.*, 1995, 60, 1391–1407.
Cicala et al., *J. Org. Chem.*, 1982, 47, 2670–2673.
Curci et al., *J. Org. Chem.*, 1980, 45, 4758–4760.
Besse et al., *Tetrahedron*, 1994, 50, 8885–8927.
Curci et al., *J. Chem. Soc.*, 1984, 155–156.
Curci et al., *Tet. Lett.*, 1995, 36, 5831–5834.
Brown et al., *Tetrahedron*, 1995, 51, 3587–3606.
Denmark et al., *J. Org. Chem.*, 1997, 62, 8288–8289.
Yang et al., *J. Am. Chem. Soc.*, 1996, 118, 491–492.
Yang et al., *J. Am. Chem. Soc.*, 1996, 118, 11311–11312.
Armstrong et al., *Tetrahedron: Asymmetry*, 1997, 8, 1677–1684.
Song et al., *Tetrahedron: Asymmetry*, 1997, 8, 2921–2826.
Aggarwal et al., *Chem. Commun.*, 1996, 191–192.
Davis et al., *Tet. Lett.*, 1986, 27, 5079–5082.
Ebrahim et al., *Tetrahedron: Asymmetry*, 1997, 8, 3163–3173.
Kroutil et al., *J. Chem. Soc., Perkin Trans. I*, 1996, 2837–2844.
Kroutil et al., *Chem. Commun.*, 1996, 845–846.
Itsuno et al., *J. Org. Chem.*, 1990, 55, 6047–6049.
Tipson et al., *Carbohyd. Res.*, 1971, 16, 383–393.
DuPenhoat et al., *Carbohyd Rest.*, 1979, 71, 135–148.
Chughtal et al., Abstracts, 1996, 212th ACS National Meetings, *Am. Chem. Soc.*
McDonald, *Mech., Mol. Migr.*, 1971, 3, 67.
Soloway et al., *J. Am. Chem. Soc.*, 1954, 76, 2941.
Leeds et al., *J. Am. Chem. Soc.*, 1954, 76, 2943.
Gardner, *J. Am. Chem. Soc.*, 1956, 78, 3421.
Johnson et al., *J. Am. Chem. Soc.*, 1957, 79, 1991.
Shine et al., *J. Am. Chem. Soc.*, 1958, 80, 2434.
House et al., *J. Org. Chem.*, 1961, 26, 3729.
Attenburrow et al., *J. Am. Chem. Soc.*, 1961, 4547.
Williamson et al., *J. Org. Chem.*, 1961, 26, 4563.
Nambara et al., *J. Org. Chem.*, 1962, 27, 2131.
Draper et al., *J. Org. Chem.*, 1962, 27, 2727.
Riehl et al., *Bull. Soc. Chim. Fr.*, 1963, 224.
Rhone, *Tet. Lett.*, 1965, 1395.
Williamson et al., *J. Org. Chem.*, 1967, 32, 3934.
McDonald et al., *J. Am. Chem. Soc.*, 1967, 89, 6573.
Smith et al., *J. Org. Chem.*, 1992, 57, 6379.
Zhu et al., *J. Am. Chem. Soc.*, 1999, 121, 4080.
Feng et al., *J. Am. Chem. Soc.*, 1999, 121, 11002.
Zhu, *J. Org. Chem.*, 2001, 66, 1818.
Williamson et al., *J. Org. Chem.*, 1967, 32(12), 3934–7.
Adam et al., *J. Am Chem. Soc.*, 1998, 120, 708–714.
*Tetrahedron*, 1962, 18, 763–765.
*J. Org. Chem.* 1997, 62, 188–193.

* cited by examiner

Primary Examiner—Deborah C. Lambkin
(74) Attorney, Agent, or Firm—Townsend and Townsend and Crew LLP

(57) ABSTRACT

A method for producing an epoxide from an olefin using a mixture hydrogen peroxide, a nitrile compound and a ketone is disclosed.

36 Claims, 2 Drawing Sheets

EPOXIDATION OF OLEFINS

CROSS-REFERENCES TO RELATED APPLICATIONS

This application claims the benefit of U.S. Provisional Application No. 60/148,904, filed Aug. 13, 1999.

STATEMENT AS TO RIGHTS TO INVENTIONS MADE UNDER FEDERALLY SPONSORED RESEARCH AND DEVELOPMENT

The U.S. Government has a paid-up license in this invention and the right in limited circumstances to require the patent owner to license others on reasonable terms as provided for by the terms of Grant No. GM55704 awarded by the National Institutes of Health.

FIELD OF THE INVENTION

The present invention is directed to epoxidation of olefins using a mixture of a ketone and hydrogen peroxide.

BACKGROUND OF THE INVENTION

Epoxidation of an olefin is one of the most useful synthetic reactions in the field of organic chemistry. Such reaction has been used frequently in the preparation of an intermediate and/or the final product of many pharmaceutically active compounds. With the recognition of the importance of a compound's stereochemistry in its pharmaceutical activity, chiral epoxidation of an olefin has become particularly desirable.

Asymmetric epoxidation of olefins presents a powerful strategy for the synthesis of enantiomerically enriched epoxides. Great success has been achieved in the epoxidation of allylic alcohols, unfunctionalized cis-olefins, and conjugated trisubstituted olefins. Among many other powerful epoxidation methods chiral dioxiranes generated in situ from Oxone® (potassium peroxymonosulfate) and a chiral ketone have appeared to be promising reagents for asymmetric epoxidations. Since the first asymmetric epoxidation of olefins with dioxirane were reported in 1984, significant progress has been made in the area. A $C_2$ symmetric cyclic chiral ketone derived from 1,1'-binaphthyl-2,2'-dicarboxylic acid has been used as a catalyst to achieve high enantioselectivity for the epoxidation of trans-4,4'-disubstituted stilbenes. Variety of other chiral ketones have been disclosed by others, for example, see Denmark and Wu, Synlett. 1999, 847, which is incorporated herein by reference in its entirety. Recently, the epoxidation of trans-disubstituted or trisubstituted olefins with high enantiomeric excess has been reported in commonly assigned PCT Publication No. WO 98/15544, which is incorporated herein by reference in its entirety.

As mentioned above, typically epoxidation of an olefin using a ketone and an oxidizing agent uses Oxone® as the oxidizing agent. The active component of Oxone® is believed to be potassium peroxymonosulfate. However, Oxone® contains other non-active salts. Often, these non-active salts must be removed after the epoxidation reaction, thereby increasing the time and cost of purifying the epoxide product. Moreover, typically an epoxidation reaction using a ketone and Oxone® requires a large volume of solvent.

Therefore, there is a need for a method of epoxidizing an olefin using a ketone and an oxidizing agent which does not require a large volume of reaction solvent. There is a need for a method of epoxidizing an olefin using a ketone and an oxidizing agent which does not require the use of Oxone®.

There is also a need for a method of epoxidizing a variety of olefins using a ketone and an oxidizing agent which does not contain a significant amount of non-active salt impurities.

SUMMARY OF THE INVENTION

Present invention provides a method for producing an epoxide from an olefin. The method involves mixing a reaction mixture comprising the olefin, hydrogen peroxide, a nitrile compound and a ketone under conditions sufficient to produce the epoxide.

The reaction mixture can also include a base. The pH of the reaction mixture is preferably from about pH 5 to about pH 14, more preferably at pH of from about pH 10 to about pH 14, and most preferably from about pH 10 to about pH 12.

In one particular embodiment of the present invention, the ketone is a chiral ketone which allows stereoselective epoxidation of the olefin. Preferably, the chiral ketone is selected from the group consisting of compounds of the formula:

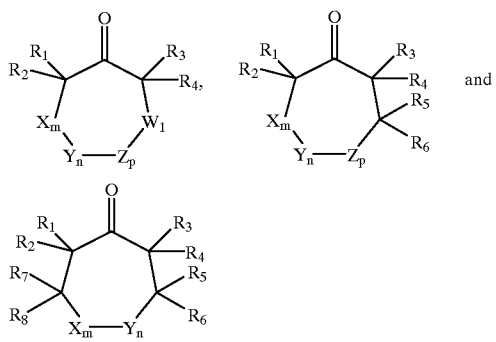

wherein

W, X, Y and Z are independently $CR_9R_{10}$, O, $NR_{11}$, S, Se, Si or P;

l, m, n and p are independently an integer from 0 to 3;

$R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxylate, ester, amino, sulfinyl, sulfonyl, sulfate, sulfite, phosphate or phosphite groups containing from 1 to about 20 carbon atoms, or two or more of $R_1$, $R_2$, $R_3$, $R_4$, $R_5$, $R_6$, $R_7$, $R_8$, $R_9$ and $R_{10}$ are linked together to form 3 to about 10 membered cyclic moiety containing 1 to about 20 carbon atoms; and $R_{11}$ is hydrogen, oxygen or alkyl, sulfonyl, alkoxy or carbonyl groups containing from 1 to about 20 carbon atoms.

More preferably, the chiral ketone is selected from the group consisting of the compound of the formula:

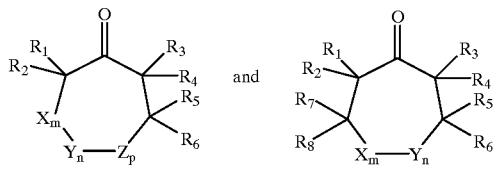

wherein preferably, m is 0, Y is O or $CR_9R_{10}$, n and p are 1, and Z is $CR_9R_{10}$.

Preferably, two or more of $R_1$, $R_2$, $R_3$, $R_4$, $R_5$, $R_6$, $R_7$, $R_8$, $R_9$ and $R_{10}$ are linked together to form 3 to about 10 membered cyclic moiety containing 1 to about 20 carbon atoms, more preferably $R_1$ and $R_2$ together form a moiety of the formula:

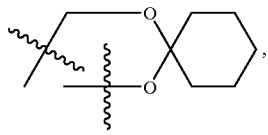

—O—C(CH$_2$CH$_3$)$_2$—O—CH$_2$— or —O—C(CH$_3$)$_2$—O—CH$_2$—.

Alternatively, $R_1$ and $R_7$ together form a moiety of the formula:

—O—C(CH$_3$)$_2$—O—, —O—C(CH$_2$CH$_3$)$_2$—O—, or —C(CH$_3$)$_2$—.

Preferably, $R_3$ and $R_6$ together form a moiety of the formula:

—O—C(CH$_3$)$_2$—O—or —O—C(CH$_2$CH$_3$)$_2$—O—.

Preferably, $R_4$, $R_5$, $R_9$ and $R_{10}$ are independently hydrogen, halide or alkoxy, carboxyl or alkyl groups having 1 to about 20 carbon atoms. More preferably, $R_4$, $R_5$ and $R_{10}$ are hydrogen and $R_9$ is hydrogen, halide, or alkoxy, carboxyl, sulfinyl or alkyl groups having 1 to about 20 carbon atoms.

Preferably, the chiral ketone is derived from a carbohydrate, quinic acid or carvone. More preferably, the chiral ketone is derived from a group consisting of carvone, inositol, quinic acid, (D)-fructose, (L)-fructose, (D)-arabinose, (L)-arabinose and (L)-sorbose.

DETAILED DESCRIPTION

Figure 1:
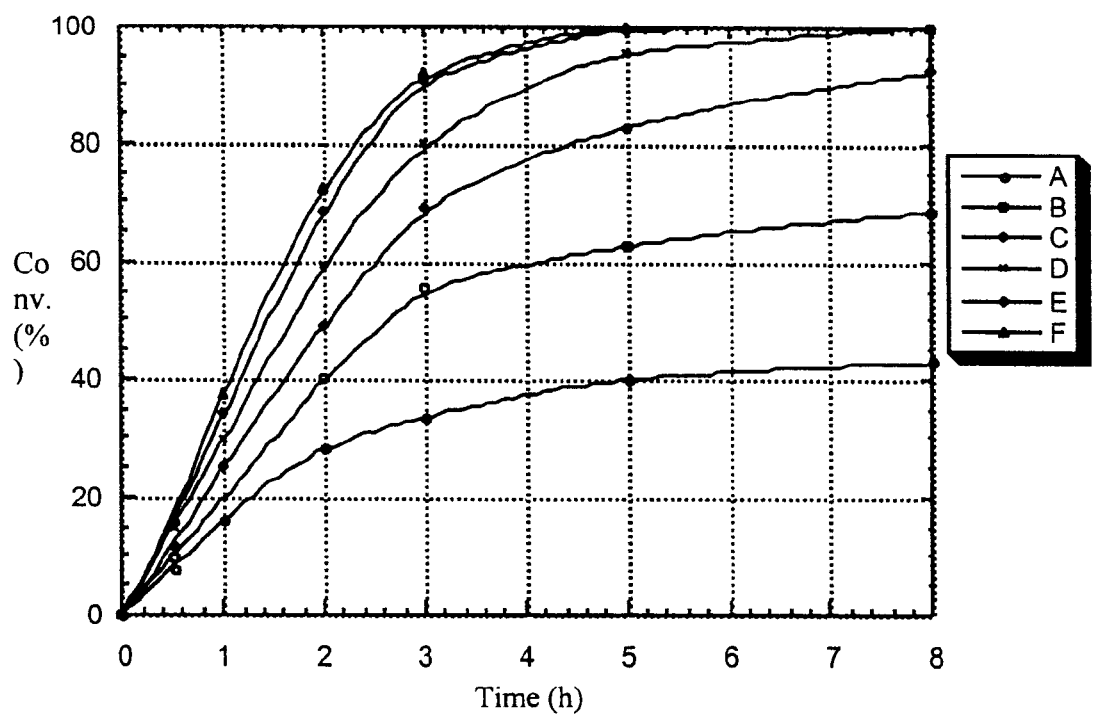
FIG. 1 is a plot of conversion of trans-β-methylstyrene against reaction time (h) at various potassium carbonate concentrations.

Epoxides are used in many industrial processes as building blocks for the synthesis of or as the final product of complex molecules such as polymers, surfactants, pesticides, insecticides, insect hormones, insect repellants, pheromones, food flavoring, and drugs. The present invention provides a method for producing an epoxide from an olefin by subjecting a reaction mixture which includes a ketone compound, hydrogen peroxide, a nitrile compound and an olefin compound to conditions sufficient to produce the epoxide from the olefin.

As used in this invention, an "olefin" refers to a compound having an alkene functionality, i.e., a double bond between two carbon atoms. An olefin can have more than one double bond. If more than one double bond is present on the olefin, the double bonds can be conjugated or non-conjugated. The olefin can be monosubstituted, di-substituted, tri-substituted or fully substituted. By substituted, it is meant that the olefinic carbon atom is attached to an atom other than hydrogen atom. For example, the olefinic carbon can be substituted with a halogen atom, silicon atom, another carbon atom, oxygen atom, sulfur atom and/or a metal atom such as lithium, sodium or magnesium. Preferably, the olefin is at least a di-substituted olefin. The di-substituted olefin can be geminal, cis-, or trans-substituted olefin. Preferably the di-substituted olefin is a trans-substituted olefin. Generally for olefins having at least three substituent groups, trans-olefin designation refers to the trans relationship between the larger substituents attached to the two different olefinic carbon atoms, whereas cis designation refers to the cis relation between the larger substituents. In addition to cis- and trans-notations, an "E" or "Z" notation can also be used to denote the relative priority of the substituent groups. E- and Z-notations denoting the stereoisomers of alkenes are well known to one of ordinary skill in the art. Preferably, the olefin is E-stereoisomer.

Preferably, the concentration of the olefin in the reaction mixture is from about 0.01 mole/liter (M) to about 5 M, more preferably from about 0.1 M to about 1 M, and most preferably from about 0.2 M to about 0.5 M.

Unlike most other ketone catalyzed epoxidation reactions which typically uses Oxone® as the oxidizing agent to generate a dioxirane in situ, the present invention uses hydrogen peroxide as the oxidizing agent. This offers a number of significant improvements over the currently known methods. For example, using Oxone® requires a relatively large volume of solvent because Oxone® is only sparingly soluble in a solvent. In addition, Oxone®, whose active ingredient is potassium peroxymonosulfate, contains impurities such as potassium bisulfate and potassium sulfate. These impurities contribute to insolubility of Oxone® in a solvent; moreover, these impurities need to be removed from the reaction mixture. All these shortcomings of using Oxone® as the oxidizing agent is avoided in the present invention by using hydrogen peroxide (typically 30% solution in water) as the oxidizing agent.

While a large excess of hydrogen peroxide (relative to the amount of olefin) can be used, generally from about 1 equiv. to about 10 equiv. of hydrogen peroxide is used, preferably from about 1 equiv. to about 5 equiv., and more preferably from about 3 equiv. to about 5 equiv.

Without being bound by any theory, it is believed that using hydrogen peroxide in combination with the nitrile compound (e.g., $R_{12}$—CN) generates the imidoperacid of the formula:

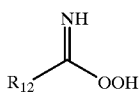

It is believed that this imidoperacid reacts with the ketone to generate the corresponding dioxirane which then epoxidizes the olefin to produce the corresponding epoxide.

The nitrile compound can be any compound containing a nitrile functional group (i.e., —CN functional group). Preferably, the nitrile compound does not contain other functional group which may react with other components of the reaction mixture. More preferably, the nitrile compound is of the formula $R_{12}$—CN, where $R_{12}$ is $C_1$–$C_{10}$ alkyl, C3–C10 cycloalkyl, $C_6$–$C_{20}$ aryl, $C_7$–$C_{21}$ aralkyl. Preferably $R_{12}$ is $C_1$–$C_6$ alkyl or $C_6$–$C_{15}$ aryl, and more preferably $R_{12}$ is methyl, ethyl, or phenyl (i.e., $R_{12}$—CN is acetonitrile, propionitrile, and benzonitrile respectively). Most preferred nitrile is acetonitrile.

Alkyl groups according to the present invention are aliphatic hydrocarbons which can be straight or branched carbon atom chain groups. Alkyl groups optionally can be substituted with one or more substituents, such as halo, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, -butyl, t-butyl, n-pentyl, heptyl, octyl, hydroxymethyl, hydroxy ethyl, chloromethyl, aminomethyl and dimethylaminomethyl.

Cycloalkyl groups are cyclic hydrocarbons, which can be subsituted with one or more substituents, such as halo, aryl, hydroxy, alkoxy, carboxy, oxo and alkyl. There may be optionally inserted along the cycloalkyl ring moiety one or more oxygen, sulfur or substituted or unsubstituted nitrogen atoms.

The nitrile compound can be used as a solvent or it can be used as a reagent. When using the nitrile compound as a reagent, typically from about 1 equiv. to about 20 equiv., relative to the amount of olefin, is used, preferably from about 1 equiv. to about 10 equiv., and more preferably from about 2 equiv. to about 4 equiv.

It should be appreciated that other hydrogen peroxide (or oxidizing agent) activators can be used in addition to or in place of the nitrile compound. Exemplary activators which may be useful include diimides such as 1,3-dicyclohexylcarbodiimide (DCC); isocyanates; chloroformates cyanate, carbonyl bitriazoles, carbonyldiimidazoles, acetals, ortho esters, orthocarbonates, acid chlorides, anhydrides, aldehydes, formamide, benzeneseleninic acid, Vilsmeier reagent, phosphinic anhydrides and other phosphorus electrophiles, and organosulfonic acids and derivatives thereof.

It should also be appreciated that instead of hydrogen peroxide, other oxidizing agents capable of producing an imidoperacid from the corresponding nitrile compound can also be used. However, for economical reasons, both in terms of the cost and purification process, hydrogen peroxide is the preferred oxidizing agent. Exemplary oxidizing agents which may be used in place of hydrogen peroxide include, but are not limited to, organic oxidizing agents and inorganic oxidizing agents, such as sodium percarbonate. Non-organic oxidizing agents (i.e., a compound that does not contain any carbon atom) are particularly preferred as these oxidizing agents and their reaction products can be easily removed from the reaction mixture by a simple aqueous extraction.

The amount of hydrogen peroxide used in the present invention depends on a variety of factors including the reactivity of the ketone, olefin, and nitrile compound. Typically, however, the amount of hydrogen peroxide used is at least about 1 equiv. relative to the amount of the ketone, preferably at least about 9 equiv., and more preferably at least about 100 equiv. In a particular embodiment of the present invention, the amount of hydrogen peroxide used is less than about 10 equiv. relative to the amount of the olefin, preferably less than about 3 equiv., and more preferably about 1 equiv.

Without being bound by a theory, it is believed that reaction between the above described imidoperacid and the ketone produces a dioxirane or some other adduct which is believed to be the active species that epoxidizes the olefin. Although the dioxirane can be isolated under certain conditions, in general it is generated and used in situ. It is believed that the reaction between an olefin and the dioxirane provides an epoxide and regenerates the ketone; therefore, the ketone can be used in a catalytic amount. Thus, in one particular embodiment of the present invention, less than one equivalent of the ketone relative to the amount of olefin is used in the present invention.

When the ketone is used as a catalyst, the same molecule of ketone can be used more than once in epoxidizing an olefin. The average number of epoxidation of olefins produced by a ketone molecule is known as a catalytic turn-over number, or simply a turn-over number. Preferably the ketones of the present invention have a turn-over number of at least about 3, more preferably at least about 50 and most preferably at least about 100. Moreover, since the ketones have such a high turn-over number, the amount of the ketones required to epoxidize a given amount of olefin can be less than the stoichiometric amount, i.e., one equivalent, of the olefin. Preferably no more than about 0.3 equivalents of the ketone is used to epoxidize olefins, more preferably no more than about 0.05 equivalents, and most preferably no more than about 0.01 equivalents.

It should be appreciated that in situ generation of dioxirane from a ketone generally requires the oxidizing agent to be more reactive towards the ketone than the olefin to avoid competing oxidation of olefin by the oxidizing agent. However, when the reactivity of the oxidizing agent with the olefin is similar or greater than with the ketone then one method of providing a higher amount of reaction between the oxidizing agent and the ketone to generate the dioxirane is to use the ketone in an amount substantially more than the amount of the olefin. In these cases, the amount of ketone used is preferably at least about 3 equiv. relative to the amount of olefin, more preferably at least about 5 equiv., and most preferably at least about 10 equiv.

The pH of the reaction mixture can influence the epoxidation reaction. The pH of the reaction solution can be conveniently achieved by adding a sufficient amount of base to maintain the pH at the desired level. The base can be added separately, all at once or in portions during the reaction.

Preferably the base is selected from the group consisting of hydroxides, carbonates, bicarbonates, borates and phosphates. More preferably the base is selected from the group consisting of potassium carbonate, potassium bicarbonate, lithium carbonate, lithium bicarbonate, sodium carbonate, cesium carbonate, rubidium carbonate, sodium bicarbonate, calcium carbonate, sodium borate, sodium phosphate, potassium phosphate, lithium hydroxide, sodium hydroxide, potassium hydroxide, magnesium hydroxide and calcium hydroxide, most preferably the base is selected from the group consisting of potassium carbonate, potassium bicarbonate, sodium bicarbonate, sodium carbonate, sodium hydroxide, sodium borate, sodium phosphate, potassium phosphate and potassium hydroxide. Alternatively, the desire pH of the reaction can be more easily maintained by using a buffer solution.

Epoxidation of olefins according to the present invention can be performed in a variety of different sequences. The addition sequence of the olefin, ketone, hydrogen peroxide, nitrile compound and base (if any) can be interchanged depending on the nature of each components. Typically, however, an aqueous hydrogen peroxide solution is added to a solution comprising the ketone, olefin, nitrile compound and base.

When the ketone is an achiral ketone, the resulting epoxide from a prochiral olefin is a racemic mixture. In contrast, an enantiomerically enriched epoxide can be prepared from a prochiral olefin by using an enantiomerically enriched chiral ketone. If the olefin contains one or more chiral centers, the epoxide can be formed diastereoselectively.

In one particular embodiment of the present invention, the ketone is achiral ketone. Exemplary achiral ketones include cyclic ketones, such as cyclohexanone, cyclopentanone, cycloheptanone, cyclooctanone and derivatives thereof; acyclic ketones, such as alkyl-alkyl ketones (e.g., acetone, methyl ethyl ketone, and derivatives thereof); alkyl-cycloalkyl ketones, such as methyl cyclohexyl ketone and the like; alkyl-aryl ketones, such as methyl phenyl ketone (i.e., acetophenone) and the like; and cycloalkyl-aryl ketones, such as cyclohexyl phenyl ketone and the like. While any achiral ketone can be used in the present invention, particularly preferred ketones include, but are not limited to, acetone, trifluoroacetone, dichloroacetone, and cyclohexanone.

In one particular embodiment of the present invention the ketone is a chiral ketone, preferably an enantiomerically enriched chiral ketone, which allows production of chiral epoxides. Chiral epoxides have become increasingly important intermediates in the synthesis of enantiomerically enriched complex molecules. It is well recognized that the stereochemistry of a molecule is important in many of the properties of the molecule. For example, physiological properties of drugs having one or more chiral centers, i.e., stereochemical centers, depend on the stereochemistry of a drug's chiral center. In addition, properties of a polymer containing a chiral monomeric unit depend on the enantiomeric purity of the monomer. Thus, it is advantageous to be able to control the stereochemistry of a chemical reaction. Since an epoxide serve as an intermediate or a starting material for many chemical compounds, it is especially desirable to be able to control the stereochemistry of the epoxide formation.

Selectivity and reactivity are two important factors that need to be considered in searching for an effective epoxidation catalyst. For the synthesis of an enantiomerically enriched epoxide using a chiral ketone as a precursor to an epoxidation catalyst, ketones containing the following general features are particularly desirable: (1) having the stereogenic centers close to the reacting center, resulting in efficient stereochemical communication between substrates (i.e., the olefins) and the catalyst; (2) having the presence of fused ring(s) or a quaternary center (i.e., fully substituted carbon atom) a to the carbonyl group to minimize the epimerization of the stereogenic centers; (3) controlling possible competing approaches of an olefin to the reacting dioxirane by sterically blocking one face or using a $C_2$ or pseudo $C_2$ symmetric element. As used in this invention, a "face" means a plane or a direction in which the olefin approaches the dioxirane.

Thus, in one particular embodiment of the present invention provides a method for asymmetrically epoxidizing olefins using a chiral ketone. Preferably one stereoisomer of the epoxide is produced in at least about 50 percent excess over the other isomer, more preferably in at least about 80 percent excess, still more preferably in at least about 90 percent excess, even more preferably in at least about 95 percent excess.

A chiral center (i.e., stereochemical center, or stereogenic center) is, of course, an atom to which four different groups are attached; however, the ultimate criterion of a chiral center is nonsuperimposability on the mirror image. Facially selective, stereoselective, enantioselective or asymmetric synthetic reactions are those in which one of a set of stereoisomers is formed exclusively or predominantly.

The chiral ketones for the present invention are preferably cyclic chiral ketones having at least 3 carbon atoms in the cyclic (i.e., ring) system, more preferably at least about 4 carbon atoms in the ring system, still more preferably at least about 5 carbon atoms in the ring system, and most preferably 5 or 6 carbon atoms in the ring system. Cyclic compounds (or moieties) refer to compounds (or moieties) having a chain of atoms that does not have a terminal portion, i.e, a ring of atoms. The atoms in a cyclic compound (or moiety) can be all carbon atoms, or it can be a chain of carbon atoms which can be interrupted by an oxygen atom, sulfur atom, nitrogen atom, silicon atom, phosphorus atom, and/or any other multi-valent atoms. Although a $C_2$-symmetry can be present in the cyclic chiral ketone, a presence of a $C_2$-symmetry on the cyclic chiral ketone is not required for the present invention.

In one particular embodiment of the present invention, the chiral ketone is selected from the group consisting of compounds of the formula:

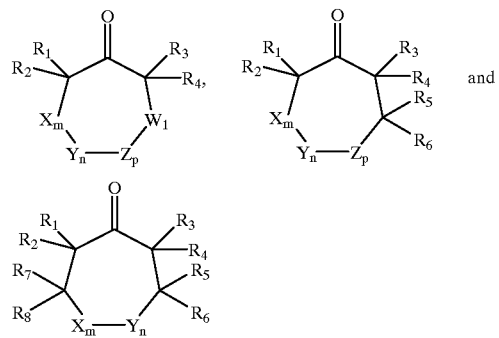

where:

W, X, Y and Z are independently $CR_9R_{10}$, O, $NR_{11}$, S, Se, Si or P;

l, m, n and p are independently an integer from 0 to 3;

$R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms; and $R_{11}$ is hydrogen, oxygen or alkyl, sulfonyl, alkoxy or carbonyl groups containing from 1 to about 20 carbon atoms. Alternatively, two or more $R_1$, $R_2$, $R_3$, $R_4$, $R_5$, $R_6$, $R_7$, $R_8$, $R_9$ and $R_{10}$ are joined (i.e., linked) to form 3 to about 10 membered cyclic moiety containing 1 to about 20 carbon atoms. For example, $R_3$ and $R_5$ can be linked to form a moiety of the formula —O—C(CH$_3$)$_2$—O—, or $R_3$ and $R_4$ can be linked together to form a moiety of the formula —O—C(CH$_2$CH$_3$)$_2$—O—(CH$_2$)—. More preferably $R_1$, $R_2$, $R_3$, $R_4$, $R_5$, $R_6$, $R_7$, $R_8$, $R_9$ and $R_{10}$ are independently hydrogen, halide, or alkoxy, siloxy, carboxyl, or sulfonyl groups having 1 to about 20 carbon atoms, or two or more $R_1$, $R_2$, $R_3$, $R_4$, $R_5$, $R_6$, $R_7$, $R_8$, $R_9$ and $R_{10}$ are linked together to form a from about three to about six-membered cyclic moiety. Without being bound by any theory, it is believed that the reactive species in the epoxidation of the olefin is the corresponding dioxiranes.

The chiral cyclic ketones can be derived from any appropriate starting material such as a carbohydrate, carvone, inositol, and quinic acid. Preferably, the chiral cyclic ketone is derived from a carbohydrate. Reasons for selecting these ketones as catalysts include (a) carbohydrates are chiral and readily available; (b) they are highly substituted with oxygen groups, which would be good for reactivity, as the inductive effect of oxygen activates the ketone catalyst; and (c) carbohydrate-derived ketones could have rigid conformations because of the anomeric effect, which would be desirable for selectivity. Preferably, the cyclic ketone is derived from an oxidation of an unprotected hydroxy group of a carbohydrate compound having at least one protected hydroxy group. As used in the present invention, carbohydrate is a sugar molecule or its derivative. Carbohydrate can be monosaccharide or polysaccharide. Exemplary carbohydrates include glucose, fructose, maltose, lactose, mannose, sorbose, ribose, xylose, rhamnose, galactose, talose, arabinose, gulose, sucrose, cellobiose, cellulose, maltonic acid, heparin, chondroitin sulfate, amylose and amylopectin. Preferably the protecting groups for protected hydroxy groups are selected from the group consisting of silyl ethers, ethers, acetals, ketals, esters, ortho esters, sulfonates, phosphates and mixtures thereof. The protecting groups for two or more hydroxy groups of the carbohydrate or its derivative can be interconnected. For example, an acetonide group protecting 4,5-hydroxy groups of fructose can be considered to be "two interconnected acetal protecting groups" since they protect two hydroxy groups on the fructose. The oxidation of a hydroxy group of a carbohydrate to form a carbonyl group is well known to one skilled in the art. See for example, Mio et al. *Tetrahedron* 1991, 47, 2133–2144. For example, pyridinium chlorochromate (PCC), pyridinium dichromate (PDC), Swern oxidation condition or other oxidizing conditions can be used to oxidize a hydroxy group of a carbohydrate or its derivative to the ketone compound of the present invention. Preferably, the carbohydrate is selected from the group consisting of fructose, sorbose, arabinose, mannose, and glucose. More preferably, the carbohydrate is selected from the group consisting of (D)-fructose, (L)-fructose (L)-sorbose, (L)-arabinose and (D)-arabinose.

Preferably, the chiral cyclic ketone is selected from the group consisting of a compound of the formula:

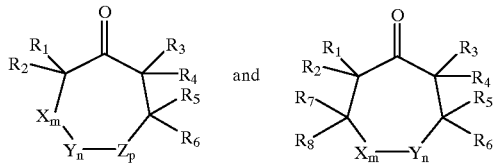

Preferably, m is 0, Y and Z are independently O or $CR_9R_{10}$, and n and p are 1. Preferably, two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms. Preferably, $R_1$ is linked with $R_2$ or $R_7$ to form a three, five or six-membered cyclic moiety. When $R_1$ and $R_2$ are linked, preferably the linkage forms a moiety of the formula:

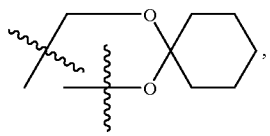

—O—C(CH₃)₂—O—CH₂—, —C(CH₃)₂—, or —O—C(CH₂CH₃)₂—O—CH₂—.

When $R_1$ and $R_7$ are linked, preferably the linkage forms a moiety of the formula —O—C(CH₃)₂—O— or —O—C(CH₂CH₃)₂—O—CH₂—. Preferably, $R_3$ and $R_6$ are linked together to form a five-membered cyclic moiety, and most preferably $R_3$ and $R_6$ are linked together to form a moiety of the formula —O—C(CH₃)₂—O—, —C(CH₃)₂— or —O—C(CH₂CH₃)₂—O—CH₂—. Preferably $R_4$, $R_5$, $R_9$ and $R_{10}$ are independently hydrogen, or alkoxy, carboxyl, sulfonyl or alkyl groups having 1 to about 20 carbon atoms. When both Y and Z are $CR_9R_{10}$, preferably one $R_9$ is hydrogen and the other $R_9$ is hydrogen, halide, alkyl or alkoxy group containing 1 to about 20 carbon atoms, more preferably 1 to about 10 carbon atoms, and most preferably 1 to about 6 carbon atoms.

As used in this invention, a moiety of the formula does not include atoms which are directly part of the parent cyclic ketone structure. Thus, for example, a compound of the formula:

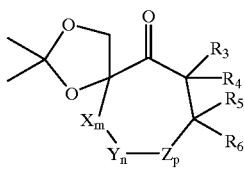

can be alternatively be described as a compound of the formula:

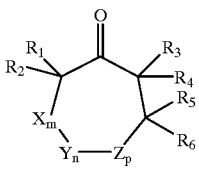

with $R_1$ and $R_2$ together forming a moiety of the formula: —O—C(CH₃)₂—O—(CH₂)—

As expected, generally the higher enantiomeric purity of the chiral ketone leads to a higher stereoselectivity of the epoxidation reaction. Therefore, for an asymmetric epoxidation, the enantiomeric excess of the chiral ketone of the present invention is preferably at least about 50% ee, more preferably at least about 80% ee, and most preferably at least about 90% ee.

For the asymmetric epoxidation, another issue that needs to be considered is the side reaction. As used in this invention, a "side reaction" is a reaction that does not ultimately lead to a production of a desired product (a desired product of the reaction between an oxidizing agent and a ketone is a dioxirane, whereas the desired product of the reaction between a dioxirane and an olefin is an epoxide). Without being bound by a theory, it appears that the Baeyer-Villiger reaction is one of the major side reactions of the ketone at pH of from about pH 7 to about pH 8. The competing Baeyer-Villiger reaction can be reduced at a higher pH which can lead to a more efficient formation of the dioxirane.

In the present invention, it has been found that higher pH generally provides a higher conversion rate of the olefin to the epoxide (i.e, higher yield of epoxides from olefins) and higher catalytic efficiency (i.e., higher turn-over rate). The pH has a profound effect on the amount of epoxide produced by the methods of the present invention. In one particular embodiment of the present invention, the pH of the reaction mixture is at least about pH 5, more preferably at least about pH 8, still more preferably at least about pH 10. Even more preferably the pH is from about pH 5 to about pH 14, yet even more preferably from about pH 10 to about pH 14, and most preferably from about pH 10 to about pH 12.

The reaction time generally affects both the yield of the epoxide as well as the enantiomeric excess of the epoxide product. Thus, in many cases while a longer reaction period typically provides higher yield of the epoxide, the enantiomeric excess begins decrease after awhile. Therefore, obtaining a maximum yield of the epoxide while maintaining a sufficient level of enantiomeric excess requires a compromise between the two diametrically opposed results. Preferably, the reaction time is from about 0.1 h to about 48 h, more preferably from about 0.1 h to about 24 h, and most preferably from about 0.1 h to about 10 h.

Another factor which determines the yield of epoxide and/or enantioselectivity of the reaction is the solvent system used. Typically, in addition to water which is present in hydrogen peroxide, any suitable organic solvent can be used as a cosolvent. Exemplary organic solvents which are useful in the present invention include, but are not limited to, nitriles such as acetonitrile, propionitrile and benzonitrile, dimethoxymethane (DMM), dimethoxyethane (DME), ethers such as tetrahydrofuran (THF) and ether, dichloromethane, chloroform, ethyl acetate, hexane, benzene, toluene, xylenes, dioxane, dimethyl formamide (DMF), pentane, alcohols including, but not limited to, methanol, ethanol, butanol and i-propyl alcohol, and mixtures thereof. Preferably, the organic solvent is selected from the group consisting of acetonitrile, DMM, DME, DMF, dioxane, butanol and mixtures thereof.

In another embodiment of the present invention, a mixture of organic solvent and aqueous solution is used as a reaction solution. A wide variety of solvents can be used for the present invention. Percentage of enantiomeric excess (% ee), which is a measure of enantioselectivity, is equal to % of one enantiomer (e.g. stereoisomer)—% of the other enantiomer. Thus for example, if the reaction produces (R,R) and (S,S) epoxides in 99% and 1%, respectively, the enantiomeric excess percentage (% ee) will be 98%. Preferably, the methods of the present invention provides asymmetric epoxidation of olefins in at least about 50% ee, more preferably at least about 80% ee, and most preferably at least about 90% ee. In another embodiment of the present invention, the yield of the epoxide from asymmetric epoxidation of an olefin is at least about 10%, more preferably at least about 50%, and most preferably at least about 80%.

The temperature of the reaction also affects the yield of the reaction and enantioselectivity of the epoxide. Generally, a lower reaction temperature requires a longer reaction time but results in higher enantioselectivity. Preferably the reaction temperature is less than about 100° C., more preferably less than about 30° C., and most preferably at about 0° C.

The present invention is useful for providing an epoxide from a variety of olefins. High enantiomeric excess can be obtained especially with trans-substituted olefins. The olefins can bear a wide range of groups, such as tert-butyl silyl (TBS) ether, trityl, acetal, chloride, and ester. Trisubstituted olefins also provide high selectivity.

The methods of the present invention can also be used for epoxidation of cis-disubstituted and terminal olefins.

The size of substituent group on the olefin often effects the % ee of the epoxide product. For example, in tri-substituted olefins of a general structure:

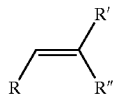

decreasing the size of R' increases the % ee. And increasing the size of R also increases the % ee. Simultaneously decreasing the size of R' and increasing the size of R further enhances the % ee.

The methods of the present invention can also be used in regio- and enantioselective monoepoxidation of conjugated polyenes. A "polyene" is a compound which has more than one unsaturated bonds including dienes, trienes and enynes. Using the methods of the present invention, monoepoxidation of polyenes can be achieved by the use of an appropriate amount of the ketone as a catalyst. If both olefins in a diene are disubstituted, regioselectivity can be controlled by using steric and/or electronic effects. The presence of an electron withdrawing group results in formation of the distal epoxide as the major product. And allylic withdrawing groups such as an acetate which is not conjugated to the olefin can also substantially deactivate the proximal olefin by the inductive effect. The regioselectivity can also be effected by steric hindrance. Steric hindrance can be used to control the formation of a single monoepoxide from a polyene compound. When a diene contains a disubstituted and a trisubstituted olefins, the epoxidation occurs selectively on the trisubstituted olefin.

One of the advantages of the present invention is availability of relatively inexpensive starting materials for producing chiral ketones. For example, chiral ketones can be easily synthesized in high overall yield from readily available carbohydrates such as fructose and sorbose as disclosed in the above mentioned commonly assigned PCT Publication No. WO 98/15544. In addition, chiral ketones of the present invention can also be synthesized from other inexpensive and readily available compounds such as carvone, inositol, and quinic acid. Some of the chiral ketones which can be easily prepared from readily available starting materials and their representative epoxidation of olefins are also disclosed in the above mentioned commonly assigned PCT Publication No. WO 98/15544.

The epoxidation methods of the present invention are environmentally friendly. Water is used as a cosolvent and unlike other current asymmetric epoxidation no toxic metals are involved. Therefore, no special disposal method is required, which significantly reduces the overall cost of the present invention.

Additional objects, advantages, and novel features of this invention will become apparent to those skilled in the art upon examination of the following examples thereof, which are not intended to be limiting.

EXAMPLES

Example 1

This example illustrates the asymmetric epoxidation of a variety of olefins using a mixture of hydrogen peroxide and a nitrile compound as the oxidizing agent for the chiral ketone 1, and the effect of variety of solvents on the epoxide yield.

A solution of the olefin (1 mmol), ketone 1 (0.3 mmol), hydrogen peroxide (30%, 0.5 mL, 5 mmol) in CH$_3$CN (2 mL)-buffer (AcOH-K$_2$CO$_3$) (the buffer pH was adjusted to 10.3 by adding HOAc to 0.1 M K$_2$CO$_3$) (1 mL) was stirred at room temperature for 2 h, a 40% conversion was obtained. Analysis of the epoxide product using chiral GC (Chiraldex G-TA) showed 86% ee. The fact that the epoxide was formed with good enantioselectivity appeared to suggest that the dioxirane had indeed been formed. However, when the reaction was carried out in other solvents, such as DMF, THF, CH$_2$Cl$_2$, EtOH, or dioxane, instead of CH$_3$CN, only trace amounts of the epoxide (<1%) were detected by GC, suggesting that hydrogen peroxide itself could not effectively generate the dioxirane and that CH$_3$CN acted as an activator. Without being bound by any theory, it is believed that in the case of CH$_3$CN, the actual oxidant responsible for the formation of the dioxirane was peroxyimidic acid 2 (eq. 2). Asymmetric epoxidation also occurred when other nitrites such as CH$_3$CH$_2$CN, CH$_3$CH$_2$CH$_2$CN were used.

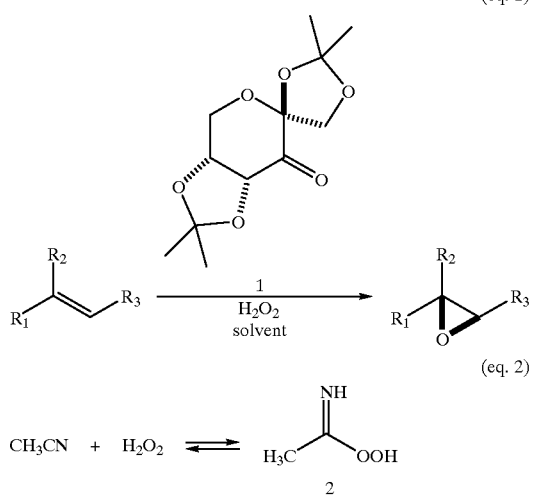

(eq. 1)

(eq. 2)

Example 2

This example illustrates the effect pH on the yield and the reaction kinetics of epoxidation using a mixture of hydrogen peroxide and a nitrile compound as the oxidizing agent for the chiral ketone 1.

Using trans-β-methylstyrene as the olefin, procedure of Example 1 was followed using a various amount of K$_2$CO$_3$. The results of potassium carbonate at 0.05 M, 0.1 M, 0.4 M, 0.6 M, 0.8 M and 1.0 M are plotted as shown in FIG. 1. High conversion of the olefin to the epoxide was obtained when the sufficient amount of potassium carbonate was used. When potassium carbonate was above 0.6 M, over 90% ee of the epoxide was obtained.

In FIG. 1, the curves presented are: (A) 0.05 M K$_2$CO$_3$ in $4\times10^{-4}$ M of EDTA (pH 11.1), (B) 0.1 M K$_2$CO$_3$ in $4\times10^{-4}$ M of EDTA (pH 11.3), (C) 0.4 M K$_2$CO$_3$ in $4\times10^{-4}$ M of EDTA (pH 11.6), (D) 0.6 M K$_2$CO$_3$ in $4\times10^{-4}$ M of EDTA (pH 11.7), (E) 0.8 M K$_2$CO$_3$ in $4\times10^{-4}$ M of EDTA (pH 11.8), (F) 1.0 M K$_2$CO$_3$ in $4\times10^{-4}$ M of EDTA (pH 11.9) (The pH indicated above is the pH of the K$_2$CO$_3$ solution. The pH varied upon adding other reaction components as well as the reaction time. This variation became smaller when higher concentration of K$_2$CO$_3$ was used).

Further studies showed that this epoxidation system could also be extended to other substrates, obtaining good yields and ee's in each case (Table 1).

TABLE 1

Asymmetric Epoxidation of Olefins Catalyzed by Ketone 1, using H$_2$O$_2$ and acetonitrile mixture as the oxidizing agent.

| Entry | Substrate | Yield (%) | ee (%) | Configuration |
|---|---|---|---|---|
| 1 | Ph⧸⧹ | 84 | 92 | (R,R) |
| 2 | Ph⧸⧹Ph | 77 | 98.7 | (R,R) |
| 3 | Ph⧸⧹OTBS | 74 | 93 | (R,R) |
| 4 | Ph⧸⧹OH | 55 | 89 | (R,R) |
| 5 | Ph-cyclohexenyl | 90 | 95 | (R,R) |

TABLE 1-continued

Asymmetric Epoxidation of Olefins Catalyzed by Ketone 1, using $H_2O_2$ and acetonitrile mixture as the oxidizing agent.

| Entry | Substrate | Yield (%) | ee (%) | Configuration |
|---|---|---|---|---|
| 6 | cyclooctenyl-OBz | 75 | 93 | (R,R) |
| 7 | cyclohexenyl-C≡C-TMS | 93 | 95 | (R,R) |
| 8 | diene-CO$_2$Et | 76 | 95 | (R,R) |

Example 3

This example illustrates a representative asymmetric epoxidation procedure (Table 1, entry 1) at 1.0 M $K_2CO_3$.

To a solution of trans-β-methylstyrene (0.118 g, 1 mmol) and ketone 1 (0.077 g, 0.3 mmol) in $CH_3CN$ (2 mL) was added a solution of 1.0 M $K_2CO_3$ in $4\times10^{-4}$ M of EDTA (1 mL) followed by $H_2O_2$ (30%, 0.3 mL, 3 mmol) at 0° C. Upon stirring at 0° C. for 7 h, the reaction mixture was quenched with hexane (5 mL), extracted with hexane, washed with saturated $Na_2S_2O_3$ and brine, dried ($Na_2SO_4$), filtered, concentrated, and purified by chromatography (silica gel was buffered with 1% $Et_3N$ in hexane, using hexane-ether as eluent) to afford the epoxide product as a colorless oil (0.113 g, 84% yield, 92% ee).

Example 4

This example illustrates effect of ketone on the epoxidation reaction.

Using the procedure of Example 2, only 1% conversion of the olefin to the epoxide was obtained after 5 h at 0° C. in the absence of chiral ketone 1. However, under similar conditions 61% conversion of the olefin to the epoxide was obtained using acetone instead of the chiral ketone 1. Therefore, other ketones can be used as a catalyst for the epoxidation of olefins.

Example 5

This example illustrates the effect of a nitrile compound on the epoxidation reaction.

In the absence of acetonitrile, using other organic solvents, such as dimethylformamide (DMF), tetrahydrofuran (THF), methylene chloride, ethanol or dioxane, epoxidation of an olefin was carried out using the procedure of Example 1. In all cases only a trace amount (<1%) of the epoxide was detected by gas chromatography. This indicates that hydrogen peroxide itself could not effectively oxidize the ketone to generate the dioxirane.

Example 6

This example illustrates the effect of pH on epoxidation of olefins with non-chiral ketones.

Figure 2:
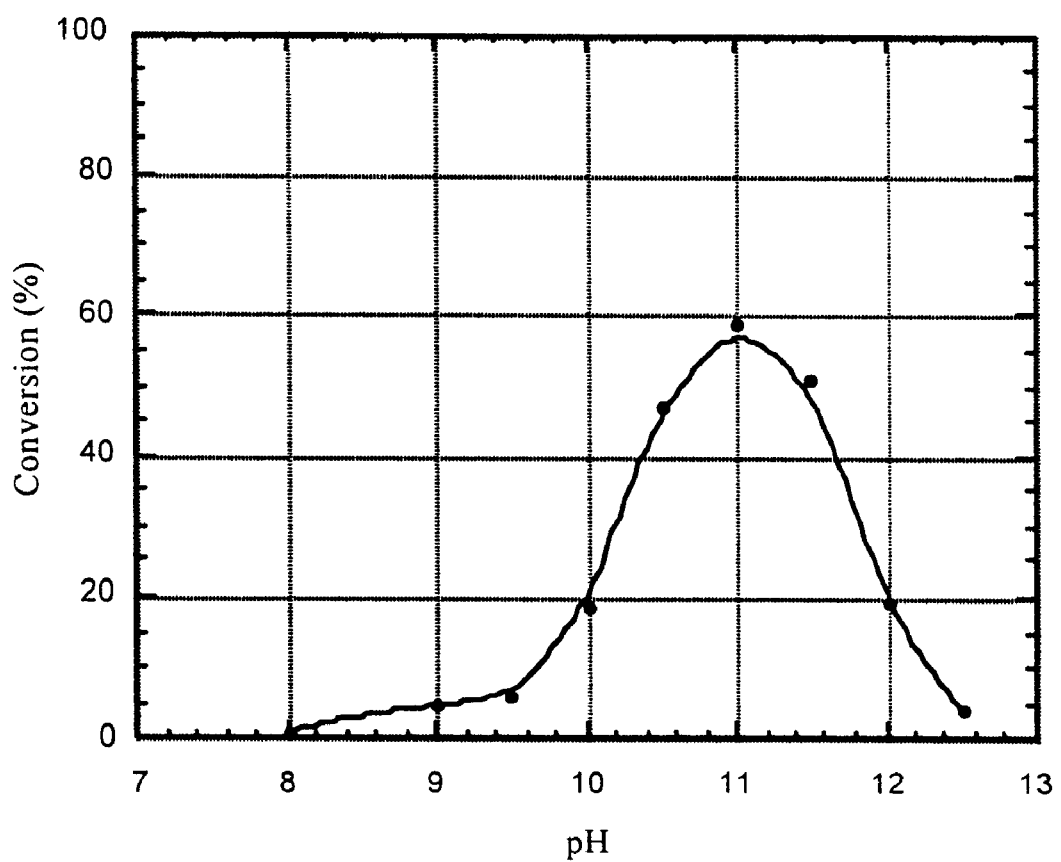
FIG. 2 is a plot of conversion of trans-β-methylstyrene against pH using CF$_3$COCH$_3$ as catalyst (5 mol %).

Procedure of Example 2 was repeated using a variety of non-chiral ketones as possible catalysts. In one particular experiment, the pH effect was further investigated using trifluoroacetone ($CF_3COCH_3$). The reaction was run in a 1:1 mixture of $CH_3CN$ and aqueous EDTA solution ($4\times10^{-4}$ M) using trans-β-methylstyrene (1 mmol) as substrate and 5 mol % $CF_3COCH_3$ as catalyst. The reaction pH was adjusted by adding $K_2CO_3$ or AcOH, and monitored by a pH meter. In one particular experiment, reactions were carried out with trans-β-methylstyrene (1 mmol), ketone (0.05 mmol) and $H_2O_2$ (4 mmol) in $CH_3CN$ (1.5 mL) and aqueous EDTA ($4\times10^{-4}$ M) (1.5 mL) at 0° C. for 10 hours. Conversions were determined by GC. As shown in FIG. 2, it was found that the ketone gave the best conversions at pH around 11.0. In the absence of ketone catalyst, the epoxidation was minimal at high pH both at 0° C. and room temperature. However, at low pH (around 8–9) substantial amount of epoxidation occurred at room temperature but not at 0° C.

Example 7

This example illustrates the effect of various ketones on the epoxidation reaction of an olefin.

A number of ketones were investigated as an epoxidation catalyst using trans-β-methylstyrene as substrate using the general procedure of Example 2. In all cases, 30 mol % ketones were used and the reactions were stopped after 10 hours. As shown in Table 2, among these ketones tested, trifluoroacetone ($CF_3COCH_3$) showed the highest activity. A complete conversion of substrate was obtained under the reaction conditions. The high efficiency displayed by this $CF_3COCH_3$—$H_2O_2$—$CH_3CN$ system suggested that this could provide a valuable epoxidation procedure. For less active ketones, higher conversions could be obtained by using more ketones and/or with prolonged reaction times.

TABLE 2

Epoxidation of trans-β-Methylstyrene Using Different Ketones[a]

| Entry | Ketone | Cat (eq.) | T(° C.) | t (h) | Conv. (%) |
|---|---|---|---|---|---|
| 1 | cyclic ketone, n = 1 | 0.3 | 0 | 10 | 5 |
| 2 | n = 2 | 0.3 | 0 | 10 | 20 |
| 3 | n = 3 | 0.3 | 0 | 10 | 2 |
| 4 | tetrahydropyran-4-one | 0.3 | 0 | 10 | 15 |
| 5 | ninhydrin/indanetrione | 0.3 | 0 | 10 | 8 |
| 6 | CH₃COCO₂R, R = Me | 0.3 | 0 | 10 | 1 |
| 7 | R = Na | 0.3 | 0 | 10 | 8 |
| 8 | acetone | 0.3 | 0 | 10 | <1 |
| 9 | ClCH₂COCH₂Cl | 0.3 | 0 | 10 | 46 |
| 10 | $F_3C$-CO-$CH_3$ | 0.3 | 0 | 10 | 100 |

[a]All reaction were carried out with trans-β-methylstyrene (1 mmol), ketone (0.3 mmol) and $H_2O_2$ (4 mmol) in $CH_3CN$ (1.5 mL) and aqueous $K_2CO_3$ solution (1.5 M in 4 × 10⁻⁴ M EDTA) (1.5 mL) at 0° C. for 10 hours. Conversions were determined by GC.

Example 8

This example illustrates the effect of epoxidation reaction on various olefins.

Using the procedure similar to that of Example 2, the epoxidation was carried out at apparent pH around 11.0, which could be easily obtained by using a 1.5 M $K_2CO_3$ aqueous solution. The reaction was run at 0° C. to slow down the decomposition of $H_2O_2$ and the peroxyimidic intermediate. As shown in Table 3, a variety of terminal, cyclic, acyclic, trans-, cis- and trisubstituted olefins have been epoxidized with good yields. Functional groups such as hydroxy, TMS, ester, and alkynes can be tolerated under this reaction condition. For those more reactive substrates, the epoxidation was completed using 10 mol % ketone within 4 hours. For those less reactive substrates, 30 mol % ketone was required to gain a high conversion. For substrates like trans-stilbene and trans-7-tetradecene with poor solubility (Table 3, entries 2 and 6), the epoxidation did not give a reasonably high conversion when $CH_3CN$ was used as the organic solvent. However, a good conversion could be obtained by running the epoxidation in a mixed solvent of $CH_3CN$-DMM (½, v/v).

TABLE 3

Epoxidations of Olefins Using $H_2O_2$ as Oxidant and $CF_3COCH_3$ as Catalyst

| Entry | Substrate | Cat. (mol %) | Yield (%) |
|---|---|---|---|
| 1 | Ph-CH=CH-CH₃ | 10 | 93 |
| 2 | Ph-CH=CH-Ph | 30 | 89 |
| 3 | Ph-CH=CH-CH₂OH | 30 | 84 |
| 4 | trans-alkenol (OH) | 10 | 64 |
| 5 | trans-alkenol (OH) | 10 | 70 |
| 6 | n-C₆H₁₃-CH=CH-C₆H₁₃-n | 30 | 94 |
| 7 | cis-alkenol | 30 | 76 |
| 8 | 1,2-dihydronaphthalene | 10 | 83 |
| 9 | cyclooctene | 10 | 70 |
| 10 | 1-phenylcyclohexene | 10 | 86 |
| 11 | 1-(TMS-ethynyl)cyclohexene | 10 | 81 |
| 12 | cyclooctenyl-OBz | 10 | 80 |
| 13 | α-methylstyrene (Ph-C(CH₃)=CH₂) | 10 | 81 |

TABLE 3-continued

Epoxidations of Olefins Using H$_2$O$_2$ as Oxidant and CF$_3$COCH$_3$ as Catalyst

| Entry | Substrate | Cat. (mol %) | Yield (%) |
|---|---|---|---|
| 14 | n-C$_8$H$_{17}$—CH=CH$_2$ | 30 | 89 |

Example 9

This example illustrates a representative epoxidation procedure using CF$_3$COCH$_3$.

Trans-stilbene oxide (Table 3, entry 2). To a mixture of suspension of trans-stilbene (18.02 g, 0.1 mol) and CF$_3$COCH$_3$ (3.36 g, 0.03 mol) in CH$_3$CN-DMM (½ v/v, 750 mL) and aqueous K$_2$CO$_3$ (1.5 M in 4×10$^{-4}$ M EDTA, 150 mL) was added H$_2$O$_2$ (30%, 40 mL, 0.4 mol) at 0° C. Upon stirring at 0° C. for 1 h and at room temperature for 5 h, the reaction mixture was extracted with hexane (3×500 mL). The combined organic layers were washed with aqueous Na$_2$S$_2$O$_3$ (1 M) (3×50 mL) and brine (100 mL), dried (Na$_2$SO$_4$), filtered, concentrated, and purified by flash chromatography on silica gel (buffered with 1% NEt$_3$) using hexane-ether as eluent to give trans-stilbene oxide as a white solid (18.3 g, 93.3%).

α-Methylstyrene Oxide (Table 3, entry 13). To a mixture of α-methylstyrene (11.8 g, 0.1 mol) and CF$_3$COCH$_3$ (1.12 g, 0.01 mol) in CH$_3$CN (150 mL) and aqueous K$_2$CO$_3$ (1.5 M in 4×10$^{-4}$ M EDTA, 150 mL) was added H$_2$O$_2$ (30%, 40 mL, 0.4 mol) at 0° C. Upon stirring at 0° C. for 3 h, the reaction mixture was extracted with hexane (3×300 mL). The combined organic layers were washed with aqueous Na$_2$S$_2$O$_3$ (1 M) (3×50 mL) and brine (100 mL), dried (Na$_2$SO$_4$), filtered, concentrated, and purified by flash chromatography on silica gel (buffered with 1% NEt$_3$) using hexane-ether as eluent to give a-methylstyrene as a colorless liquid (10.8 g, 80.6%).

Example 10

This example illustrates epoxidation of olefins using acetone.

Acetone is a cheap and readily available ketone. Although its activity is much lower than trifluoroacetone (see, for example, Table 2 above), it can also efficiently catalyze the epoxidation at pH around 11.0 when it is used in excess. For example, an 80% yield of 1-phenylcyclohexene oxide was obtained when the epoxidation was carried out using >20 eq. of acetone for 24 h.

Unlike CF$_3$COCH$_3$, which gives higher conversion at high pH, acetone catalyzed epoxidation reactions proceeded at much faster rate at a lower pH (about 8.3). Because the decomposition of H$_2$O$_2$ was not very fast at this pH, the reaction can be done at room temperature. Although controlled experiment showed that significant amount of epoxidation also occurred in the absence of acetone at this pH (Payne epoxidation), the addition of acetone allowed the epoxidation to proceed much faster and gave higher conversion. For example, a 41% conversion of trans-β-methylstyrene was obtained in the absence of acetone after stirred at room temperature for 10 h. However, in the presence of acetone, an 83% yield of trans-β-methylstyrene oxide could be obtained after stirring for 5 h. Table 4 lists additional examples using acetone under similar conditions.

TABLE 4

Epoxidation of Olefins Using Acetone at pH Around 8.3

| Entry | Substrate | Time (h) | Yield (%) |
|---|---|---|---|
| 1 | Ph—CH=CH—CH$_3$ | 5 | 83 |
| 2 | Ph—CH=CH—CH$_2$OH | 12 | 82 |
| 3 | cyclooctene | 5 | 70 |
| 4 | 1-phenylcyclohexene | 5 | 90 |
| 5 | Ph—C(=CH$_2$)CH$_3$ | 5 | 69 |
| 6 | n-C$_8$H$_{17}$—CH=CH$_2$ | 12 | 90 |

Example 11

This example illustrates a representative epoxidation procedure using CH$_3$COCH$_3$.

At high pH (around 11.0). To a solution of 1-phenylcyclohexene (0.158 g, 1 mmol) in CH$_3$CN (1.5 mL) and acetone (2.0 mL, 27 mmol) was added aqueous K$_2$CO$_3$ (1.5 M in 4×10$^{-4}$ M EDTA, 1.5 mL) and H$_2$O$_2$ (30%, 0.4 mL, 4 mmol) at 0° C. Upon stirring at 0° C. for 24 h, the reaction mixture was extracted with hexane, washed with aqueous Na$_2$S$_2$O$_3$ and brine, dried (Na$_2$SO$_4$), filtered, concentrated, and purified by chromatography on silica gel (buffered with 1% NEt$_3$) to give the epoxide as a colorless oil (0.139 g, 80%).

At low pH (around 8.3) (Table 4, entry 1). To a mixture of trans-β-methylstyrene (0.118 g, 1 mmol) and CH$_3$COCH$_3$ (2.0 mL, 27 mmol) in CH$_3$CN (1.5 mL) and aqueous K$_2$CO$_3$ (0.05 M in 4×10$^{-4}$ M EDTA, 1.0 mL) was added H$_2$O$_2$ (30%, 0.4 mL, 4 mmol). Upon stirring at room temperature for 5 h, the reaction mixture was extracted with hexane or ether. The combined extracts were washed with aqueous Na$_2$S$_2$O$_3$ (1 M) and brine, dried (Na$_2$SO$_4$), filtered, concentrated, and purified by flash chromatography on silica gel (buffered with 1% NEt$_3$) to give the epoxide product as a colorless oil (0.111 g, 83% yield).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing an epoxide from an olefin comprising the steps of providing a reaction mixture comprising hydrogen peroxide, a nitrile compound, a ketone compound, and an olefin compound under conditions sufficient to produce an epoxide from said olefin.

2. The method of claim 1, wherein said nitrile compound is of the formula $R_{12}$—CN, wherein $R_{12}$ is $C_1$–$C_{10}$ alkyl, $C_3$–$C_{10}$ cycloalkyl, $C_6$–$C_{20}$ aryl, or $C_7$–$C_{21}$ aralkyl.

3. The method of claim 2, wherein said nitrile compound is acetonitrile, propionitrile, and benzonitrile.

4. The method of claim 1, wherein said ketone is achiral ketone.

5. The method of claim 4, wherein said ketone compound is acetone, trifluoroacetone, dichloroacetone, or cyclohexanone.

6. The method of claim 1, wherein said ketone is a chiral ketone.

7. The method of claim 6, wherein said method produces said epoxide stereoselectively.

8. The method of claim 7, wherein said epoxide is produced in at least about 80% ee.

9. The method of claim 6, wherein said chiral ketone is selected from the group consisting of compounds of the formula:

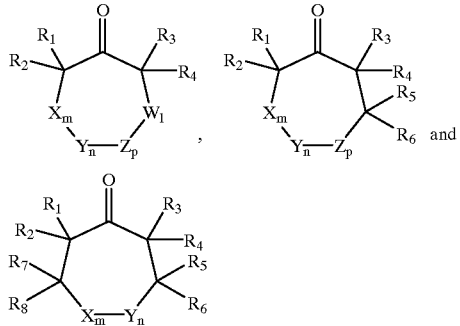

wherein

W, X, Y and Z are independently $CR_9R_{10}$, O, $NR_{11}$, S, Se, Si or P;

l, m, n and p are independently an integer from 0 to 3;

$R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms; and $R_{11}$ is hydrogen, oxygen or alkyl, sulfonyl, alkoxy or carbonyl groups containing from 1 to about 20 carbon atoms.

10. The method of claim 1, wherein said reaction mixture further comprises a base.

11. The method of claim 10, wherein said base is selected from the group consisting of potassium carbonate, potassium bicarbonate, sodium bicarbonate, sodium carbonate, sodium hydroxide, sodium borate, sodium phosphate, potassium phosphate and potassium hydroxide.

12. The method of claim 10, wherein said reaction mixture has pH of from about pH 5 to about pH 14.

13. The method of claim 1, wherein said reaction mixture is at a temperature of less than about 30° C.

14. The method of claim 1, wherein said reaction mixture further comprises a reaction solvent selected from the group consisting of acetonitrile, dimethoxyethane, water, dimethyl formamide, dimethoxymethane, dioxane, butanol, and mixtures thereof.

15. A method for asymmetric epoxidation of an olefin comprising the step of providing a reaction mixture comprising hydrogen peroxide, a nitrile compound, a chiral ketone and said olefin under conditions sufficient to produce enantiomerically enriched epoxide.

16. The method of claim 15, wherein said chiral ketone is selected from the group consisting of compounds of the formula:

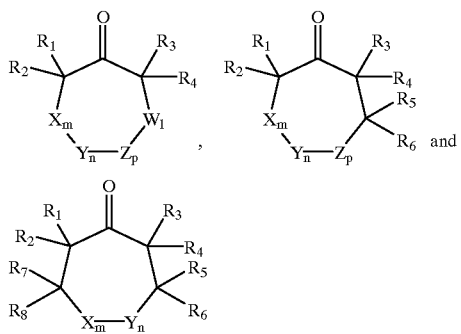

wherein

W, X, Y and Z are independently $CR_9R_{10}$, O, $NR_{11}$, S, Se, Si or P;

l, m, n and p are independently an integer from 0 to 3;

$R_1$, $R_2$, $R_3$, $R_4$, $R_5$, $R_6$, $R_7$, $R_8$, $R_9$ and $R_{10}$ are independently hydrogen, halide, hydroxyl, nitro, thio, or alkyl, alkoxy, aryl, silyl, siloxy, carbonyl, carboxyl, ester, amino, sulfinyl, sulfonyl, sulfate, sulfite, phosphate or phosphite groups containing from 1 to about 20 carbon atoms, or two or more $R_1$, $R_2$, $R_3$, $R_4$, $R_5$, $R_6$, $R_7$, $R_8$, $R_9$ and $R_{10}$ are linked to form 3 to about 10 membered cyclic moiety containing 1 to about 20 carbon atoms; and $R_{11}$ is hydrogen, oxygen or alkyl, sulfonyl, alkoxy or carbonyl groups containing from 1 to about 20 carbon atoms.

17. The method of claim 15, wherein said nitrile compound is acetonitrile, propionitrile, or benzonitrile.

18. The method of claim 16, wherein said chiral ketone is a compound of the formula:

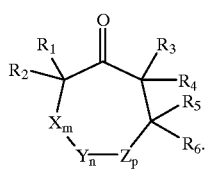

19. The method of claim 18, wherein m is 0, Y is O or $CR_9R_{10}$, n and p are 1, and Z is $CR_9R_{10}$.

20. The method of claim 19, wherein two or more of $R_1$, $R_2$, $R_3$, $R_4$, $R_5$, $R_6$, $R_9$ and $R_{10}$ are linked together to form 3 to about 10 membered cyclic moiety containing 1 to about 20 carbon atoms.

21. The method of claim 20, wherein $R_1$ and $R_2$ together form a moiety of the formula:

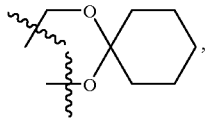

—O—(CH$_2$CH$_3$)$_2$—O—CH$_2$— or —O—C(CH$_3$)$_2$—O—CH$_2$—.

22. The method of claim 21, wherein $R_1$ and $R_2$ together form a moiety of the formula:

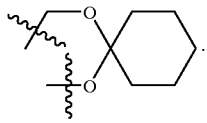

23. The method of claim 21, wherein $R_1$ and $R_2$ together form a moiety of the formula —O—C(CH$_3$)$_2$—O—CH$_2$— or —O—C(CH$_2$CH$_3$)$_2$—O—CH$_2$—.

24. The method of claim 19, wherein $R_3$ and $R_6$ together form a moiety of the formula —O—C(CH$_3$)$_2$—O— or —O—C(CH$_2$CH$_3$)$_2$—O—.

25. The method of claim 24, wherein $R_4$, $R_5$, $R_9$ and $R_{10}$ are independently hydrogen, halide, or sulfinyl, alkoxy, carboxyl or alkyl groups having 1 to about 20 carbon atoms.

26. The method of claim 16, wherein said chiral ketone is of the formula:

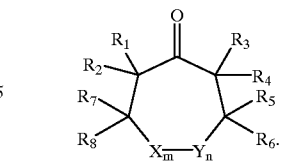

27. The method of claim 26, wherein m is 0, Y is $CR_9R_{10}$, and n is 1.

28. The method of claim 27, wherein two or more of $R_1$, $R_2$, $R_3$, $R_4$, $R_5$, $R_6$, $R_7$, $R_8$, $R_9$ and $R_{10}$ are linked together to form 3 to about 10 membered cyclic moiety containing 1 to about 20 carbon atoms.

29. The method of claim 28, wherein $R_1$ and $R_7$ together form a moiety of the formula —O—C(CH$_3$)$_2$—O— or —O—C(CH$_2$CH$_3$)$_2$—O—.

30. The method of claim 29, wherein $R_3$ and $R_6$ together form a moiety of the formula —O—C(CH$_3$)$_2$—O— or —O—C(CH$_2$CH$_3$)$_2$—O—.

31. The method of claim 30, wherein $R_4$, $R_5$, $R_9$ and $R_{10}$ are independently hydrogen, halide, or sulfinyl, alkoxy, sulfonyl, carboxyl or alkyl groups having 1 to about 20 carbon atoms.

32. The method of claim 28, wherein $R_1$ and $R_7$ together form a moiety of the formula —C(CH$_3$)$_2$—.

33. The method of claim 15, wherein said reaction mixture has pH of from about pH 5 to about pH 14.

34. The method of claim 15, wherein said reaction mixture is at a temperature of less than about 30° C.

35. The method of claim 15, wherein said reaction mixture further comprises a solvent selected from the group consisting of acetonitrile, dimethoxymethane, dimethoxyethane, water, dimethyl formamide, dioxane, butanol, and mixtures thereof.

36. The method of claim 15, wherein said epoxidation provides said epoxide in at least about 80% ee.

* * * * *